(12) United States Patent
Tsuji et al.

(10) Patent No.: US 7,491,850 B2
(45) Date of Patent: Feb. 17, 2009

(54) BISPHOSPHITE AND PROCESS FOR PRODUCING ALDEHYDE COMPOUND WITH THE BISPHOSPHITE

(75) Inventors: Tomoaki Tsuji, Kashima-gun (JP); Hideharu Iwasaki, Kurashiki (JP)

(73) Assignee: Kuraray Co., Ltd., Kurashiki (JP)

( * ) Notice: Subject to any disclaimer, the term of this patent is extended or adjusted under 35 U.S.C. 154(b) by 68 days.

(21) Appl. No.: 10/594,131

(22) PCT Filed: Mar. 22, 2005

(86) PCT No.: PCT/JP2005/005162

§ 371 (c)(1),
(2), (4) Date: Sep. 25, 2006

(87) PCT Pub. No.: WO2005/090369

PCT Pub. Date: Sep. 29, 2005

(65) Prior Publication Data

US 2007/0197834 A1 Aug. 23, 2007

(30) Foreign Application Priority Data

Mar. 23, 2004 (JP) .............................. 2004-083992

(51) Int. Cl.
*C07F 9/02* (2006.01)
*C07C 45/50* (2006.01)
(52) U.S. Cl. ........................................ 568/14; 568/454
(58) Field of Classification Search .................. 568/14, 568/454
See application file for complete search history.

(56) References Cited

U.S. PATENT DOCUMENTS

| 5,910,600 | A | * | 6/1999 | Urata et al. ................. 558/162 |
| 6,274,773 | B1 | * | 8/2001 | Gelling et al. .............. 568/454 |
| 6,570,033 | B2 | * | 5/2003 | Rottger et al. ................ 558/78 |
| 2004/0199023 | A1 | | 10/2004 | Whiteker et al. |
| 2005/0164874 | A1 | | 7/2005 | Tsuji |

FOREIGN PATENT DOCUMENTS

| EP | 0 518 241 | 12/1992 |
| JP | 10 45776 | 2/1998 |
| JP | 2001-503757 | 3/2001 |
| JP | 2004-501927 | 1/2004 |

OTHER PUBLICATIONS

Christopher J. Cobley, et al., "Synthesis and Application of a New Bisphosphite Ligand Collection for Asymmetric Hydroformylation of Allyl Cyanide", J. Org. Chem., vol. 69, pp. 4031-4040, 2004.
U.S. Appl. No. 10/594,131, filed Sep. 25, 2006, Tsuji et al.

* cited by examiner

*Primary Examiner*—Sikarl A Witherspoon
(74) *Attorney, Agent, or Firm*—Oblon, Spivak, McClelland, Maier & Neustadt, P.C.

(57) ABSTRACT

Bisphosphite(s) represented by the following general formula (I):

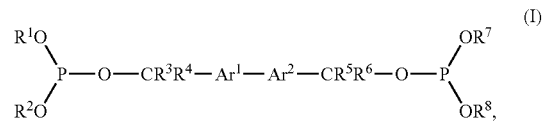

wherein $Ar^1$ and $Ar^2$ are each independently a substituted or unsubstituted arylene group; $R^1$, $R^2$, $R^7$ and $R^8$ are each independently a substituted or an unsubstituted alkyl group, a substituted or an unsubstituted aryl group or a substituted or an unsubstituted heterocyclic group, or $R^1$ and $R^2$ or $R^7$ and $R^8$ may together form a ring with their associated oxygen atoms and phosphor atom; and $R^3$, $R^4$, $R^5$ and $R^6$ are each independently a hydrogen atom or an alkyl group, with the proviso that the carbon atom bearing $R^3$ and $R^4$ and the carbon atom bearing $R^5$ and $R^6$ are bound to the respective arylene groups at the ortho position to the $Ar^1$—$Ar^2$ bond. Also provided is a process for producing aldehyde(s) using the bisphosphite and a Group 8 to 10 metal compound. A composition comprising the bisphosphite and a Group 8 to 10 metal compound is further provided.

10 Claims, No Drawings

BISPHOSPHITE AND PROCESS FOR PRODUCING ALDEHYDE COMPOUND WITH THE BISPHOSPHITE

CROSS REFERENCE TO RELATED APPLICATION

This application is a 371 of PCT/JP05/005162, filed Mar. 22, 2005 and claims priority to Japan Patent Application No. 2004-083992, filed Mar. 23, 2004.

TECHNICAL FIELD

The present invention relates to novel bisphosphites and a process for producing aldehyde(s) using the bisphosphite(s) and a Group 8 to 10 metal compound. The bisphosphites of the present invention serve as a useful component of catalysts used in the hydroformylation of olefins with carbon monoxide and hydrogen.

TECHNICAL BACKGROUND

Aldehyde(s) can be produced by reacting an olefin with carbon monoxide and hydrogen in the presence of a Group 8 to 10 metal compound or in the presence of a Group 8 to 10 metal compound and phosphorus compound(s). The process is known as "hydroformylation" or "oxo process" and is an important industrial process widely used in the production of aldehyde(s).

The hydroformylation generally involves catalysts based on a rhodium compound or a combination of a rhodium compound and phosphorus compound(s) for industrial use. Among phosphorus compounds conventionally used in the hydroformylation are phosphines, such as tributylphosphine, trioctylphosphine, tricyclohexylphosphine, triphenylphosphine, and tri(p-tolyl)phosphine (See, for example, Japanese Patent Laid-Open Publication No. Hei 8-10624); monophosphites, such as triphenylphosphite, tri-n-butylphosphite, and tris(2-t-butyl-4-methylphenyl)phosphite (See, for example, *The Journal of Organic Chemistry*, Vol. 34, No. 2 (1969): pp. 327-330; *Journal of the Chemical Society, Chemical Communications* (1991): pp. 1096-1097); bisphosphites, such as bis[3,3',5,5'-tetra-t-butyl(1,1'-biphenyl)-2,2'-diyl]-1,2-ethyldiphosphite, bis[3,3',5,5'-tetra-t-butyl(1,1'-biphenyl)-2,2'-diyl]-2,7,9,9-tetramethyl-9H-xanthine-4,5-diyldiphosphite, and bis[3,3'-di-t-butyl-5,5'-dimethoxy(1,1'-biphenyl)-2,2'-diyl]-2,7,9,9-tetramethyl-9H-xanthine-4,5-diyldiphosphite (See, for example, *Organometallics* Vol. 15 (1996): pp. 835-847; *Helvetica Chimica Acta* Vol. 84 (2001): pp. 3269-3280). Different hydroformylation processes have been developed that make use of these phosphorus compounds.

DISCLOSURE OF THE INVENTION

Problems to be Solved by the Invention

A drawback of the hydroformylation using conventional rhodium compound(s) and phosphorus compound(s) above written is that the active catalytic species tend to lose their activities in the course of the reaction under the high-pressure and high-temperature environment (for example, 10 MPa, 150° C.). However, carrying out the reaction under milder conditions (for example, 3 MPa, 80° C.) leads to decreased catalytic activity that must be compensated by larger quantities of rhodium compound(s) and phosphorus compound(s) such as monophosphite(s) and bisphosphite(s). This inevitably adds to the production cost. Thus, there still remains a large margin for improvement in the performance of the phosphorus compounds used in the hydroformylation.

Accordingly, it is an object of the present invention to provide a novel bisphosphite for use in hydroformylation of olefins that not only achieves high selectivity, but can also maintain its high catalytic activity under relatively mild conditions as well as to provide a process for producing aldehydes using the bisphosphite(s).

Means for Solving the Problems

In one aspect, the present invention provides bisphosphite(s) represented by the following general formula (I) (referred to simply as "bisphosphite(I)", hereinafter):

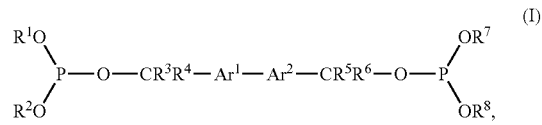

wherein $Ar^1$ and $Ar^2$ are each independently a substituted or unsubstituted arylene group; $R^1$, $R^2$, $R^7$ and $R^8$ are each independently a substituted or an unsubstituted alkyl group, a substituted or an unsubstituted aryl group or a substituted or an unsubstituted heterocyclic group, or $R^1$ and $R^2$ or $R^7$ and $R^8$ may together form a ring with their associated oxygen atoms and phosphorus atom; and $R^3$, $R^4$, $R^5$ and $R^6$ are each independently a hydrogen atom or an alkyl group, with the proviso that the carbon atom bearing $R^3$ and $R^4$ and the carbon atom bearing $R^5$ and $R^6$ are bound to the respective arylene groups at the ortho position to the $Ar^1$—$Ar^2$ bond.

In another aspect, the present invention provides a process for producing aldehyde(s), comprising reacting an olefin with carbon monoxide and hydrogen in the presence of the bisphosphite(I) and a Group 8 to 10 metal compound.

In still another aspect, the present invention provides a composition containing the bisphosphite(I) and a Group 8 to 10 metal compound (the composition may be referred to as "catalyst composition," hereinafter).

BEST MODE FOR CARRYING OUT THE INVENTION

Examples of arylene group that $Ar^1$ and $Ar^2$ in the general formula each represent include phenylene group, naphthylene group, anthracylene group, 1,1'-biphenylene group and 1,1'-binaphthylene group. Such arylene groups may have substituents, and examples thereof include halogen atoms, such as fluorine atom, chlorine atom, bromine atom and iodine atom; alkyl groups preferably having 1 to 6 carbon atoms, such as methyl group, ethyl group, propyl group, isopropyl group, 1,1-dimethylpropyl group, n-butyl group, isobutyl group, s-butyl group, t-butyl group, n-pentyl group and cyclohexyl group; and alkoxyl groups preferably having 1 to 4 carbon atoms, such as methoxy group, ethoxy group, propoxy group, isopropoxy group, n-butoxy group, isobutoxy group, s-butoxy group and t-butoxy group.

The alkyl group that $R^1$, $R^2$, $R^7$ and $R^8$ each represent is preferably an alkyl group having 1 to 6 carbon atoms, such as methyl group, ethyl group, propyl group, isopropyl group, 1,1-dimethylpropyl group, n-butyl group, isobutyl group, s-butyl group, t-butyl group, n-pentyl group and cyclohexyl group. Such alkyl groups may have substituents, and examples thereof include halogen atoms, such as fluorine atom, chlorine atom, bromine atom and iodine atom; alkoxyl groups preferably having 1 to 4 carbon atoms, such as methoxy group, ethoxy group, propoxy group, isopropoxy group, butoxy group, isobutoxy group, s-butoxy group and t-butoxy group; acyl groups preferably having 2 to 4 carbon atoms, such as acetyl group, propionyl group, butyryl group and isobutyryl group; acyloxy groups preferably having 2 to 4 carbon atoms, such as acetyloxy group, propionyloxy group, butyryloxy group and isobutyryloxy group; alkoxycarbonyl groups preferably having 2 to 5 carbon atoms, such as methoxycarbonyl group, ethoxycarbonyl group, propoxycarbonyl group, isopropoxycarbonyl group, butoxycarbonyl group, isobutoxycarbonyl group, s-butoxycarbonyl group and t-butoxycarbonyl group; carboxyl group and salts thereof; and sulfonic acid group and salts thereof.

The aryl group that $R^1$, $R^2$, $R^7$, and $R^8$ each represent is preferably an aryl group having 6 to 14 carbon atoms. Examples thereof include phenyl group, naphthyl group and anthryl group. Examples of the heterocyclic groups that $R^1$, $R^2$, $R^7$ and $R^8$ each represent include 3-pyridyl group, 4-pyridyl group, 2-quinolyl group, 4-quinolyl group, 6-quinolyl group, 4-benzofuryl group and 5-benzofuryl group. These aryl groups and heterocyclic groups may have substituents, and examples thereof include halogen atoms, such as fluorine atom, chlorine atom, bromine atom and iodine atom; alkyl groups preferably having 1 to 6 carbon atoms, such as methyl group, ethyl group, propyl group, isopropyl group, 1,1-dimethylpropyl group, butyl group, isobutyl group, s-butyl group, t-butyl group, n-pentyl group and cyclohexyl group; fluoroalkyl groups preferably having 1 to 3 carbon atoms, such as difluoromethyl group, trifluoromethyl group, 1,1-difluoroethyl group, 2,2-difluoroethyl group and 1-fluoropropyl group; alkoxyl groups preferably having 1 to 4 carbon atoms, such as methoxy group, ethoxy group, propoxy group, isopropoxy group, butoxy group, isobutoxy group, s-butoxy group and t-butoxy group; acyl groups preferably having 2 to 4 carbon atoms, such as acetyl group, propionyl group, butyryl group and isobutyryl group; acyloxy groups preferably having 2 to 4 carbon atoms, such as acetyloxy group, propionyloxy group, butyryloxy group and isobutyryloxy group; alkoxycarbonyl groups preferably having 2 to 5 carbon atoms, such as methoxycarbonyl group, ethoxycarbonyl group, propoxycarbonyl group, isopropoxycarbonyl group, butoxycarbonyl group, isobutoxycarbonyl group, s-butoxycarbonyl group and t-butoxycarbonyl group; carboxyl group and salts thereof; and sulfonic acid group and salts thereof.

When $R^1$ and $R^2$ or $R^7$ and $R^8$ together form a ring structure with their associated oxygen atoms and phosphorus atom, $R^1$ and $R^2$ or $R^7$ and $R^8$ bind to each other to form a divalent organic group. Examples of such divalent organic groups include 1,2-ethylene group, 1,1,2,2-tetramethyl-1,2-ethylene group, 1,2-diphenyl-1,2-ethylene group, 1,3-propylene group, 2,2-dimethyl-1,3-propylene group, 1,1'-biphenyl-2,2'-diyl group, 3,3',5,5'-tetra-t-butyl-1,1'-biphenyl-2,2'-diyl group and 3,3'-di-t-butyl-5,5'-dimethoxy-1,1'-biphenyl-2,2'-diyl group.

The alkyl group that $R^3$, $R^4$, $R^5$ and $R^6$ each represent is preferably an alkyl group having 1 to 3 carbon atoms, for example, such as methyl group, ethyl group, n-propyl group and isopropyl group. Of these, methyl group is particularly preferred. The carbon atom bearing $R^3$ and $R^4$ and the carbon atom bearing $R^5$ and $R^6$ are bound to the respective arylene groups at the ortho position to the $Ar^1$—$Ar^2$ bond.

In one process for producing the bisphosphite(I) of the present invention, a diol compound of the following general formula (II):

$$M^1O—CR^3R^4—Ar^1—Ar^2—CR^5R^6—OM^2, \quad (II)$$

wherein $Ar^1$, $Ar^2$, $R^3$, $R^4$, $R^5$ and $R^6$ are as defined above; and $M^1$ and $M^2$ are each hydrogen atom or alkali metal, (the compound is referred to simply as "diol compound (II)", hereinafter), a halogenated phosphite of the following general formula (III):

wherein $R^1$ and $R^2$ are as defined above; and X is chlorine atom, bromine atom or iodine atom, (the compound is referred to simply as "halogenated phosphite (III)", hereinafter), and a halogenated phosphite of the following general formula (IV):

wherein $R^7$, $R^8$ and X are as defined above, (the compound is referred to as "halogenated phosphite (IV)," hereinafter. The halogenated phosphite (IV) and the halogenated phosphate (III) may have an identical structure) are reacted with each other, either at once or sequentially, in an inert gas atmosphere such as nitrogen and argon and in the presence of a solvent or, when $M^1$ and/or $M^2$ in the diol compound (II) is hydrogen atom, in the presence of a solvent and a base (the process is referred to as "bisphosphite production process A," hereinafter) (See, for example, *Organometallics*, vol. 15 (1996): pp. 835-847). We now look further into this process.

The diol compound (II), one of the starting materials for the production of the bisphosphite(I), can be obtained in the following manner when $M^1$ and $M^2$ are each hydrogen atom and $R^3$, $R^4$, $R^5$ and $R^6$ are also each hydrogen atom. First, 1-chloro-2-methylbenzene is reacted in an aqueous sodium hydroxide solution in the presence of catalytic amounts of polyethylene glycol and palladium carbon to give 2,2'-dimethylbiphenyl. The reaction is carried out in a hydrogen atmosphere for 2 to 4 hours at 90 to 120° C. under 405 kPa (see, for example, *Tetrahedron*, vol. 55 (1999): pp. 14763-14768). The alkyl groups (methyl groups) of 2,2'-dimethylbiphenyl are then oxidized with potassium permanganate to convert the product into a carboxylic acid, which in turn is reduced with lithium aluminum hydride at 0° C. to give the desired diol compound (II) (see, for example, Example 1 described in U.S. Pat. No. 4,694,109).

Examples of the alkali metal that $M^1$ and $M^2$ each represent include lithium atom or sodium atom. The diol compound (II) with $M^1$ and $M^2$ each being an alkali metal may be produced by any proper technique. For example, the diol compound (II) with $M^1$ and $M^2$ each being hydrogen atom may be reacted with 1.8 to 4 molar equivalents, with respect to the diol compound (II), of a metal hydride, such as sodium hydride and potassium hydride, or an alkyllithium, such as methyllithium and n-butyllithium, at −80 to 25° C. under atmospheric pressure in the presence of a solvent such as hexane and tetrahydrofuran.

The halogenated phosphate (III) and the halogenated phosphate (IV), the other starting materials required for the production of the bisphosphite(I), can be obtained in the following manner. A trihalogenated phosphorus compound represented by the general formula $PX_3$, wherein X is as defined above, is reacted with alcohols having general formulas of $R^1$OH, $R^2$OH, $R^7$OH and $R^8$OH, wherein $R^1$, $R^2$, $R^7$ and $R^8$ are as defined above. The total amount of the alcohols used is preferably 1.8 to 2 molar equivalents with respect to the trihalogenated phosphorus compound. The reaction is carried out in an inert gas atmosphere such as nitrogen and argon at a reaction temperature of −100 to 100° C., under a reaction pressure of 0.05 to 3 MPa, and if necessary, in the presence of a base such as triethylamine and pyridine and a solvent such as hexane, cyclohexane, benzene and dimethyl ether.

In the above-described "bisphosphite production process A" for producing the bisphosphite(I), it is preferred that the halogenated phosphites (III) and (IV) are each used in an amount of 0.8 to 1.2 molar equivalents with respect to the diol compound (II). When the halogenated phosphites (III) and (IV) have an identical structure, it is preferred that the total amount of the halogenated phosphites (III) and (IV) is from 1.6 to 2.4 molar equivalents with respect to the diol compound (II).

Examples of the solvent for use in the bisphosphite production process A include saturated aliphatic hydrocarbons, such as pentane, hexane, heptane, octane, nonane, decane and cyclohexane; aromatic hydrocarbons, such as benzene, toluene, ethylbenzene, propylbenzene, o-xylene, m-xylene, p-xylene, o-ethyltoluene, m-ethyltoluene and p-ethyltoluene; and ethers, such as diethyl ether, dipropyl ether, diisopropyl ether, butyl methyl ether, t-butyl methyl ether, dibutyl ether, tetrahydrofuran and tetrahydropyran. These solvents may be used either individually or in combination of two or more. When used, the solvent is preferably used in an amount of 1 to 90 mass % with respect to the entire reaction mixture, though it may be used in any proper amount.

Examples of the base that is used in the bisphosphite production process A when $M^1$ and/or $M^2$ in the diol compound (II) is hydrogen atom include nitrogen-containing compounds, such as triethylamine, tri-n-butylamine, tri-n-octylamine, diethylisopropylamine, N-methylpyrrolidine, N-methylpiperidine, N-methylmorpholine, N,N-dimethylaniline, pyridine, picoline, collidine, lutidine and quinoline; and alkali metal carbonates and bicarbonates, such as lithium carbonate, sodium carbonate, potassium carbonate, lithium bicarbonate, sodium bicarbonate and potassium bicarbonate. These bases may be used either individually or in combination of two or more. When used, the amount of the base is preferably from 0.8 to 3 molar equivalents with respect to the total amount of $M^1$ and $M^2$ that are each hydrogen atom.

The bisphosphite production process A is typically carried out at a reaction temperature of −100 to 100° C. and under a reaction pressure of 0.05 to 3 MPa (gauge pressure).

In the bisphosphite production process A, the diol compound (II), the halogenated phosphite (III) and the halogenated phosphite (IV) can be reacted with each other using any suitable technique. When $M^1$ and $M^2$ in the diol compound (II) are each hydrogen atom, the diol compound (II) may be added to a mixture of the halogenated phosphite (III) and the halogenated phosphate (IV) in the presence of the base, or alternatively, the halogenated phosphite (III) and the halogenated phosphate (IV) are added to the diol compound (II), either at once or sequentially, in the presence of the base.

The bisphosphite(I) can be separated/purified from the resulting reaction mixture by common techniques used in the separation/isolation of organic compounds. For example, the crystallized salt, which is by-product, is removed from the reaction mixture by filtration and the solvent is evaporated from filtrate. The resultant crude product is then subjected to column chromatography, distillation, recrystallization or other separation/purification techniques to obtain the desired bisphosphite(I) at high purity.

We will now describe a process for producing aldehyde(s) by reacting an olefin with carbon monoxide and hydrogen (Hydroformylation) in the presence of the bisphosphite(I) and a Group 8 to 10 metal compound. The process is referred to as "Process 1", hereinafter.

The olefin for use in Process 1 may be either a straight-chained, branched or cyclic olefin. Examples of such olefins include ethylene, propylene, 1-butene, isobutene, 1-pentene, 1-hexene, 1-heptene, 1-octene, 1-nonene, 1,6-octadiene, 1,7-octadiene, vinylcyclohexene, cyclooctadiene, dicyclopentadiene, cyclopentene, cyclohexene, 1-methylcyclohexene, cyclooctene, limonene, allyl alcohol, crotyl alcohol, 3-methyl-3-buten-1-ol, 7-octen-1-ol, 2,7-octadien-1-ol, vinyl acetate, allyl acetate, methyl acrylate, ethyl acrylate, methyl methacrylate, methyl vinyl ether, allyl ethyl ether, 5-hexenamide, acrylonitrile, 7-octenal, 1-methoxy-2,7-octadiene, 1-ethoxy-2,7-octadiene, 1-propoxy-2,7-octadiene, 1-isopropoxy-2,7-octadiene, styrene, α-methylstyrene, β-methylstyrene and divinylbenzene.

The Group 8 to 10 metal compound may be a rhodium compound, cobalt compound, ruthenium compound or iron compound and so on. Examples of rhodium compound include $Rh(acac)(CO)_2$, $RhCl(CO)(PPh_3)_2$, $RhCl(MA_3$, $RhBr(CO)(PPh_3)_2$, $Rh_4(CO)_{12}$ and $Rh_6(CO)_{16}$. Examples of cobalt compound include $HCo(CO)_3$, $HCo(CO)_4$, $CO_2(CO)_8$ and $HCo_3(CO)_9$. Examples of ruthenium compound include $Ru(CO)_3(PPh_3)_2$, $RuCl_2(PPh_3)_3$, $RuCl_3(PPh_3)_3$ and $Ru_3(CO)_{12}$. Examples of iron compound include $Fe(CO)_5$, $Fe(CO)_4$ $PPh_3$ and $Fe(CO)_4(PPh_3)_2$. Of these compounds, rhodium compounds favor relatively mild reaction conditions and are particularly suitable for use in Process 1. $Rh(acac)(CO)_2$ is particularly preferred. The Group 8 to 10 metal compound is preferably used in an amount of 0.0001 to 1000 mmol, more preferably in an amount of 0.005 to 10 mmol (as measured by the amount of metal atom), for every 1 liter of the reaction mixture. The Group 8 to 10 metal compound used in amounts less than 0.0001 mmol for 1 liter of the reaction mixture results in a significantly decreased reaction rate, whereas the compound used in amounts greater than 1000 mmol cannot achieve correspondingly improved effects, but rather only adds to the cost of the catalyst.

The bisphosphite(I) may be used in Process 1 either individually or in combination of two or more. The amount of the bisphosphite(I) used is preferably in the range of 2 to 1000 molar equivalents (as measured by the amount of phosphorus atoms), and more preferably in the range of 4 to 500 molar equivalents with respect to the metal atoms present in the Group 8 to 10 metal compound. Even more preferably, the bisphosphite(I) is used in an amount of 10 to 200 molar equivalents (as measured by the amount of phosphorus atoms) with respect to the metal atoms present in the Group 8 to 10 metal compound to ensure high reaction rate. The bisphosphite(I) when used in amounts less than 2 molar equivalents with respect to the metal atoms present in the Group 8 to 10 metal compound results in decreased stability of the active catalyst species, whereas the bisphosphite(I) used in amounts greater than 1000 molar equivalents may lead to a significantly decreased reaction rate.

When using the bisphosphite(I) and the Group 8 to 10 metal compound, that is, a catalyst composition in Process 1, such catalyst composition can be prepared by any suitable technique. For example, the bisphosphite(I) and the Group 8 to 10 metal compound may first be mixed together, if necessary, in the presence of a solvent, to form a catalyst composition, which in turn is added to the reaction mixture for Process 1. Alternatively, the bisphosphite(I) and the Group 8 to 10 metal compound may be added at once to a mixture of an olefin and an optional solvent, which will be described later, so that producing a catalyst composition in the reaction system.

The catalyst composition obtained in the above-described manner containing the bisphosphite(I) and the Group 8 to 10 metal compound shows high catalytic activity in the hydroformylation of an olefin (Process 1). This catalyst composition can be used as a catalyst not only in Process 1 (hydroformylation), but also in hydrogenation of unsaturated bonds and formation of carbon-carbon bonds.

In Process 1, the bisphosphite(I) may be used with other phosphorus compounds. Examples of such phosphorus compounds include phosphines, such as triisopropylphosphine, tri-n-butylphosphine, tri-t-butylphosphine, tribenzylphosphine, triphenylphosphine, tris(p-methoxyphenyl)phosphine, tris(p-N,N-dimethylaminophenyl)phosphine,tris(p-fluorophenyl)phosphine, tri-o-tolylphosphine, tri-m-tolylphosphine, tri-p-tolylphosphine, tris(pentafluorophenyl) phosphine, bis(pentafluorophenyl)phenylphosphine, diphenyl(pentafluorophenyl)phosphine, methyldiphenylphosphine, ethyldiphenylphosphine, cyclohexyldiphenylphosphine, dimethylphenylphosphine, diethylphenylphosphine, 2-furyldiphenylphosphine, 2-pyridyldiphenylphosphine, 4-pyridyldiphenylphosphine, m-diphenylphosphinobenzenesulfonic acid or metal salts thereof, p-diphenylphosphinobenzoic acid or metal salts thereof, and p-diphenylphosphinophenylphosphonic acid and metal salts thereof; and phosphites, such as triethylphosphite, triphenylphosphite, tris(p-methoxyphenyl)phosphite, tris(o-methylphenyl)phosphite, tris(m-methylphenyl)phosphite, tris(p-methylphenyl)phosphite, tris(o-ethylphenyl) phosphite, tris(m-ethylphenyl)phosphite, tris(p-ethylphenyl) phosphite, tris(o-propylphenyl)phosphite, tris(m-propylphenyl)phosphite, tris(p-propylphenyl)phosphite, tris (o-isopropylphenyl)phosphite, tris(m-isopropylphenyl) phosphite, tris(p-isopropylphenyl)phosphite, tris(o-t-butylphenyl)phosphite, tris(p-t-butylphenyl)phosphite, tris (p-trifluoromethylphenyl)phosphite, tris(2,4-dimethylphenyl)phosphite, tris(2,4-di-t-butylphenyl) phosphite, and tris(2-t-butyl-4-methylphenyl)phosphite. When these phosphorus compounds are used with the bisphosphite(I), the amounts of the "phosphorus compounds" may not be strictly limited. Nonetheless, the phosphorus compounds are preferably used in an amount of 5 molar equivalents or less, and more preferably in an amount of 0.5 to 3 molar equivalents with respect to the bisphosphite(I).

Process 1 may be carried out in the presence or absence of a solvent. Examples of the solvent include saturated aliphatic hydrocarbons, such as pentane, hexane, heptane, octane, nonane, decane and cyclohexane; aromatic hydrocarbons, such as benzene, toluene, ethylbenzene, propylbenzene, butylbenzene, o-xylene, m-xylene, p-xylene, o-ethyltoluene, m-ethyltoluene and p-ethyltoluene; alcohols, such as isopropyl alcohol, isobutyl alcohol and neopentyl alcohol; ethers, such as diethyl ether, dipropyl ether, butyl methyl ether, t-butyl methyl ether, dibutyl ether, ethyl phenyl ether, diphenyl ether, tetrahydrofuran and 1,4-dioxane; and ketones, such as acetone, ethyl methyl ketone, methyl propyl ketone, diethyl ketone, ethyl propyl ketone and dipropyl ketone. These solvents may be used either individually or in combination of two or more. When the solvents are used, the amounts of them may not be limited. Nonetheless, they are typically used in an amount of 1 to 90 mass % with respect to the entire reaction mixture.

In carrying out Process 1, a gaseous mixture of carbon monoxide and hydrogen is preferably introduced to the reaction system at a molar ratio of 10:1 to 1:10 (carbon monoxide: hydrogen), and more preferably at a molar ratio of 2:1 to 1:2. Process 1 is preferably carried out under a reaction pressure of 0.01 to 10 MPa (gauge pressure), and more preferably under a reaction pressure of 0.5 to 5 MPa (gauge pressure) to ensure high reaction rate. The reaction temperature is preferably in the range of 40 to 150° C., and more preferably in the range of 70 to 130° C. to prevent the decrease in the catalytic activity.

Process 1 may be carried out by using a stirrer reactor, liquid-circulation reactor, gas-circulation reactor or bubble column reactor and may be carried out as a continuous or batch process.

If necessary, an additive may be used in Process 1 to prevent the increase the high-boiling compounds caused by the side reaction of aldehydes. Examples of the additive include triethylamine, tributylamine, tri-n-octylamine, N,N,N',N'-tetramethyl-1,2-diaminoethane, N,N,N',N'-tetramethyl-1,3-diaminopropane, N,N,N',N'-tetramethyl-1,4-diaminobutane, N,N-diethylethanolamine, triethanolamine, N-methylpiperidine, N-methylpyrrolidine, N-methylmorpholine, pyridine, picoline, lutidine, collidine and quinoline. When used, these additives are preferably added in an amount of 200 to 3000 molar equivalents, and more preferably in an amount of 800 to 2000 molar equivalents with respect to the Group 8 to 10 metal compound.

Process 1 may be carried out using any suitable technique. In one example, an olefin and, if necessary, the above-described additive are mixed together by stirring at the fixed temperature in the presence of a gaseous mixture containing carbon monoxide and hydrogen. While the mixture is being stirred, a mixture solution of the bisphosphite(I) and the Group 8 to 10 metal compound (i.e., catalyst composition) is fed.

The aldehyde(s) can be separated/purified from the resulting reaction mixture by common techniques. For example, low-boiling point components, such as the solvent, are evaporated from the reaction mixture under reduced pressure, and the residue is further purified by distillation to obtain the desired highly pure aldehyde(s). And prior to distillation, the catalyst composition may be separated from the residue by evaporation, extraction, adsorption or other separation techniques. The separated catalyst composition can be reused in the hydroformylation (Process 1).

EXAMPLES

The present invention will now be described with reference to Examples, which are not intended to limit the scope of the invention in any way. In Examples that follow, each of the processes for producing the halogenated phosphite (III) or (IV) and bisphosphite(I) is carried out in a nitrogen or argon atmosphere, and the hydroformylation is carried out in a 1:1 (molar ratio) gaseous mixture of carbon monoxide and hydrogen.

A $^1$H-NMR spectrometer (GSX-270 manufactured by JEOL Ltd.) was used for the identification of bisphosphite(I). And the reaction mixture obtained in the hydroformylation was analyzed by gas chromatography (J&W Scientific DB-1 (60 m) attached to GC-17A manufactured by SHIMADZU CORPORATION). Conditions for gas chromatography are as follows: Injection Temp.=280° C.; Temperature maintained at 160° C. for 5 min, increased at a rate of 10° C./min, then maintained at 260° C. for 20 min; Detection Temp.=280° C.

Example 1

6.6 g of phosphorus trichloride (100 mmol) and 200 mL of tetrahydrofuran were placed in a 500 mL three-necked flask equipped with a thermometer and a dropping funnel, then 23.7 g (300 mmol) of pyridine was added to the flask. After the reaction system was cooled to −70° C., 21.6 g of 2-methylphenol (200 mmol) in 100 mL of tetrahydrofuran was added dropwise while the temperature was kept within −70° C. to −60° C. Once the addition was completed, the mixture was allowed to warm to room temperature over about 1 hour. The pyridine hydrochloride, which is by-product, was removed by filtration and the low-boiling point components were evaporated from the filtrate under reduced pressure (0.01 MPa) to give 29.0 g of crude product of di(2-methylphenyl)phosphorochloridite.

29.0 g of the crude di(2-methylphenyl)phosphorochloridite obtained above, 12.0 g of pyridine (151.7 mmol) and 200 mL of tetrahydrofuran were placed in a 500 mL three-necked flask equipped with a reflux condenser, a dropping funnel, a thermometer and a magnetic stirrer. The mixture was stirred and cooled to −75 to −65° C. To this mixture, 10.7 g (49.9 mmol) of 2,2'-biphenyldimethanol in 200 mL of tetrahydrofuran was added dropwise over 1 hour while the temperature was kept within −70 to −60° C. Once the addition was completed, the mixture was stirred for another hour at the same temperature, was allowed to warm to room temperature over 1 to 2 hours, and was then stirred for another hour at 50 to 65° C. The resulting reaction mixture was allowed to cool to room temperature. Subsequently, 2 mL of methanol was added and the resultant pyridine hydrochloride was removed from the mixture by filtration. The filtrate was then concentrated under reduced pressure until the volume of the filtrate was reduced to 50 mL or less. 200 mL of toluene was then added to the condensate and the resulting pyridine hydrochloride was removed by filtration. The filtrate was again concentrated until the volume of the filtrate was reduced to 50 mL or less. The resulting condensate was purified by column chromatography (eluant; volume ratio of hexane/toluene=30/1 to 30/10) and was condensed to give 21.2 g of a bisphosphite of the following formula as colorless oil (referred to as "bisphosphite A", hereinafter) (60.5% yield with respect to 2,2'-biphenyldimethanol).

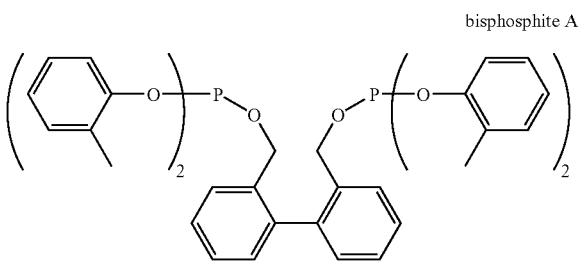

bisphosphite A $^1$H-NMR data for bisphosphite A obtained above are as follows: $^1$H-NMR (270 MHz, DMSO-$d_6$, TMS) δ: 1.93-2.04 (m, 12H); 4.88-5.05 (m, 4H); 6.76-7.53 (m, 24H).

Example 2

The same procedure was followed as in Example 1, except that 21.6 g (200 mmol) of 2-methylphenol was replaced by 27.2 g (200 mmol) of 2-isopropylphenol. The procedure gave 25.2 g of a bisphosphite of the following formula as colorless oil (referred to as "bisphosphite B", hereinafter) (66.2% yield with respect to 2,2'-biphenyldimethanol).

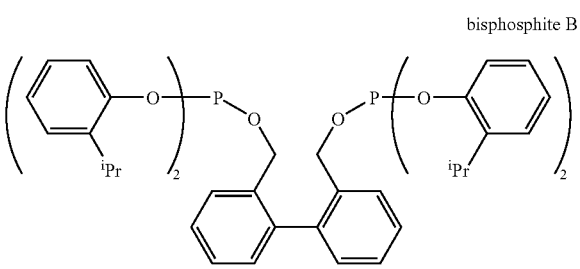

bisphosphite B $^1$H-NMR data for bisphosphite B obtained above are as follows: $^1$H-NMR (270 MHz, DMSO-$d_6$, TMS) δ: 0.81-1.10 (m, 24H); 3.96-3.14 (m, 4H); 4.90-5.06 (m, 4H); 6.71-7.61 (m, 24H).

Example 3

The same procedure was followed as in Example 1, except that 21.6 g (200 mmol) of 2-methylphenol was replaced by 30.0 g (200 mmol) of 4-t-butylphenol. The procedure gave 19.8 g of a bisphosphite of the following formula as colorless oil (referred to as "bisphosphite C", hereinafter) (48.7% yield with respect to 2,2'-biphenyldimethanol).

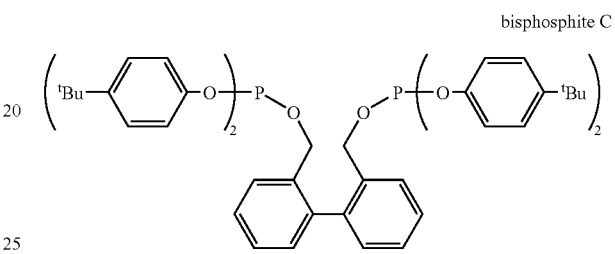

bisphosphite C $^1$H-NMR data for bisphosphite C obtained above are as follows: $^1$H-NMR (270 MHz, DMSO-$d_6$, TMS) δ: 1.22 (m, 36H); 4.78-4.93 (m, 4H); 6.78-7.60 (m, 24H).

Example 4

The same procedure was followed as in Example 1, except that 21.6 g (200 mmol) of 2-methylphenol was replaced by 24.4 g (200 mmol) of 2,6-dimethylphenol. The procedure gave 14.1 g of a bisphosphite of the following formula as colorless oil (referred to as "bisphosphite D", hereinafter) (50.1% yield with respect to 2,2'-biphenyldimethanol).

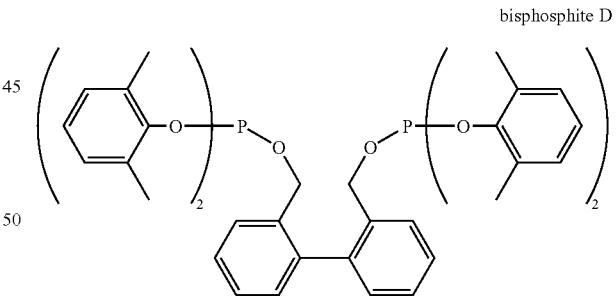

bisphosphite D $^1$H-NMR data for bisphosphite D obtained above are as follows: $^1$H-NMR (270 MHz, CDCl$_3$, TMS) δ: 2.06 (m, 24H); 4.94-5.08 (m, 4H); 6.82-7.55 (m, 20H).

Example 5

The same procedure was followed as in Example 1, except that 21.6 g (200 mmol) of 2-methylphenol was replaced by 18.8 g (200 mmol) of phenol. The procedure gave 21.5 g of a bisphosphite of the following formula as colorless oil (referred to as "bisphosphite E", hereinafter) (71.6% yield with respect to 2,2'-biphenyldimethanol).

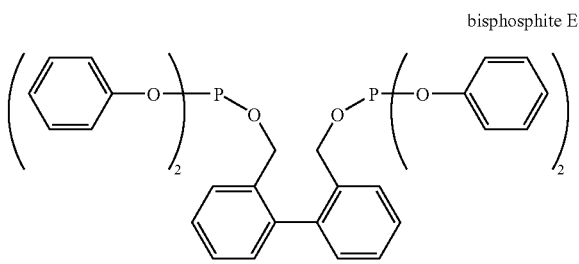

bisphosphite E $^1$H-NMR (270 MHz, DMSO-$d_6$, TMS) δ: 4.64-4.80 (m, 4H); 6.79-7.52 (m, 24H).

Example 6

Hydroformylation of 1-octene

In a 1:1 (molar ratio) gaseous mixture of carbon monoxide and hydrogen, 15.5 mg (0.06 mmol) of Rh(acac)(CO)$_2$, 421.6 mg (0.6 mmol) of bisphosphite A obtained in Example 1 and 100 mL of toluene were placed in a 100 mL three-necked flask equipped with a magnetic stirrer. The mixture was stirred at 50° C. for 30 min to make a catalyst composition. Meanwhile, 18.1 g (161.1 mmol) of 1-octene was placed in a 100 mL autoclave in a 1:1 (molar ratio) gaseous mixture of carbon monoxide and hydrogen. The autoclave had a magnetic stirrer, a gas inlet, an inlet for catalyst composition and a sampling outlet. The pressure within the autoclave and the internal temperature were set at 3.0 MPa (gauge pressure) and 125° C., respectively. 1.5 mL of the catalyst composition obtained above was fed to the autoclave under pressure at 125° C. and the mixture was stirred for 1.5 hours with the internal pressure increased to 5.0 MPa (gauge pressure). The analysis of the resulting reaction mixture by gas chromatography revealed that the conversion of 1-octene was 84.7%. The selectivity for the aldehydes resulting from the hydroformylation of the olefin (the aldehydes are referred to simply as "aldehydes", hereinafter) was 96.4% (molar ratio of 1-nonanal/2-methyloctanal=69.4/30.6). The results are shown in Table 1.

Example 7

The same procedure was followed as in Example 6, except that 421.6 mg (0.6 mmol) of bisphosphite A was replaced by 488.9 mg (0.6 mmol) of bisphosphite B. The results are shown in Table 1.

Example 8

The same procedure was followed as in Example 6, except that 421.6 mg (0.6 mmol) of bisphosphite A was replaced by 522.6 mg (0.6 mmol) of bisphosphite C. The results are shown in Table 1.

Example 9

The same procedure was followed as in Example 6, except that 421.6 mg (0.6 mmol) of bisphosphite A was replaced by 369.4 mg (0.6 mmol) of bisphosphite D. The results are shown in Table 1.

Example 10

The same procedure was followed as in Example 6, except that 421.6 mg (0.6 mmol) of bisphosphite A was replaced by 385.5 mg (0.6 mmol) of bisphosphite E. The results are shown in Table 1.

Comparative Example 1

The same procedure was followed as in Example 6, except that 421.6 mg (0.6 mmol) of bisphosphite A was replaced by 372.3 mg (1.2 mmol) of triphenylphosphite. The results are shown in Table 1.

Comparative Example 2

The same procedure was followed as in Example 6, except that 421.6 mg (0.6 mmol) of bisphosphite A was replaced by 624.8 mg (1.2 mmol) of tris(2-t-butyl-4-methyl)phosphite. The results are shown in Table 1.

TABLE 1

|  | % conversion of 1-octene | % selectivity of aldehydes | 1-nonanal/ 2-methyloctanal (molar ratio) |
|---|---|---|---|
| Example 6 | 84.7 | 96.4 | 69.4/30.6 |
| Example 7 | 82.3 | 95.4 | 70.3/29.7 |
| Example 8 | 88.1 | 94.4 | 67.3/32.7 |
| Example 9 | 85.3 | 94.1 | 69.7/30.3 |
| Example 10 | 88.5 | 92.0 | 69.1/30.9 |
| Comparative Example 1 | 75.1 | 89.3 | 57.0/43.0 |
| Comparative Example 2 | 60.9 | 88.3 | 61.3/38.7 |

The results of Examples 6 through 10 and Comparative Examples 1 and 2 indicate that the catalyst compositions for hydroformylation of 1-octene containing the bisphosphites(I) of the present invention and a Group 8 to 10 metal compound each achieve a higher conversion of an olefin into corresponding aldehydes and a higher selectivity for aldehydes which are substituted at the end of the molecule by a formyl group as compared to the catalyst compositions containing known phosphites and a Group 8 to 10 metal compound.

Example 11

Hydroformylation of 1,6-octadiene

The same procedure was followed as in Example 6, except that 18.1 g (161.6 mmol) of 1-octene and 421.6 mg (0.6 mmol) of bisphosphite A were replaced by 17.8 g (161.6 mmol) of 1,6-octadiene and 385.5 mg (0.6 mmol) of bisphosphite E obtained in Example 5, respectively. The analysis of the resulting mixture by gas chromatography revealed that the conversion of 1,6-octadiene was 84.7%. The selectivity for the compounds resulting from the hydroformylation of the carbon-carbon double bond at the end of the molecule (at position 1) was 92.3% (molar ratio of 7-nonenal/2-methyl-6-octenal=68.5/31.5, (the compounds are referred to as "terminal aldehydes 1", hereinafter)) and the selectivity for the compounds resulting from the hydroformylation of the carbon-carbon double bond at the internal of the molecule (at position 6) was 3.2% (the compounds are referred to as "internal aldehydes 1", hereinafter).

Comparative Example 3

The same procedure was followed as in Example 11, except that 385.5 mg (0.6 mmol) of bisphosphite E was replaced by 624.8 mg (1.2 mmol) of tris(2-t-butyl-4-methyl) phosphite. The analysis of the resulting mixture by gas chromatography revealed that the conversion of 1,6-octadiene was 82.3%. The selectivity for the terminal aldehydes 1 was 81.1% (molar ratio of 7-nonenal/2-methyl-6-octenal=58.9/41.1) and the selectivity for the internal aldehydes 1 was 13.2%.

The results of Example 11 and Comparative Example 3 indicate that the hydroformylation of 1,6-octadiene with the catalyst composition containing the bisphosphite(I) of the present invention and a Group 8 to 10 metal compound results in higher selectivity for compounds which are substituted at the end of the molecule by formyl group (i.e., terminal aldehydes 1) and is less likely to occur at the carbon-carbon double bond at the internal of the molecule.

Example 12

Hydroformylation of 2,7-octadien-1-ol

The same procedure was followed as in Example 6, except that 18.1 g (161.6 mmol) of 1-octene and 421.6 mg (0.6 mmol) of bisphosphite A were replaced by 20.4 g (161.6 mmol) of 2,7-octadien-1-ol and 385.5 mg (0.6 mmol) of bisphosphite E obtained in Example 5, respectively. The conversion of 2,7-octadien-1-ol was 88.1%. The selectivity for the compounds resulting from the hydroformylation of the carbon-carbon double bond at the end of the molecule (at position 7) (the compounds are referred to as "terminal aldehydes 2", hereinafter) was 91.0% (molar ratio of 9-hydroxy-7-nonenal/8-hydroxy-2-methyl-6-octenal=72.3/27.7). The selectivity for the compounds resulting from the hydroformylation of the carbon-carbon double bond at the internal of the molecule (at position 2) was 4.4% (the compounds are referred to as "internal aldehydes 2", hereinafter).

The results of Examples 11 and 12 demonstrate that the hydroformylation of 1,6-octadiene and 2,7-octadien-1-ol with the catalyst composition containing the bisphosphite(I) of the present invention and a Group 8 to 10 metal compound achieves a high conversion of the olefins into corresponding monoaldehydes under relatively mild conditions. The process also makes it possible to selectively obtain compounds resulting from the hydroformylation of the terminal carbon-carbon double bond at the end of the molecule.

Comparative Example 4

The same procedure was followed as in Example 12, except that 385.5 mg (0.6 mmol) of bisphosphite E was replaced by 624.8 mg (1.2 mmol) of tris(2-t-butyl-4-methyl)phosphite. The analysis of the resulting mixture by gas chromatography revealed that the conversion of 2,7-octadien-1-ol was 85.3%. The selectivity for the terminal aldehydes 2 was 79.3% (molar ratio of 9-hydroxy-7-nonenal/8-hydroxy-2-methyl-6-octenal=59.7/40.3) and the selectivity for the internal aldehydes 2 was 16.1%.

The results of Example 12 and Comparative Example 4 indicate that the hydroformylation of 2,7-octadien-1-ol with the catalyst composition containing the bisphosphite(I) of the present invention and a Group 8 to 10 metal compound results in higher selectivity for compounds which are substituted at the end of the molecule by formyl group (i.e., terminal aldehydes 2) and is less likely to take place at the carbon-carbon double bond at the internal of the molecule.

INDUSTRIAL APPLICABILITY

The present invention provides novel bisphosphite(s).

When a composition composes the bisphosphite(s) of the present invention and a Group 8 to 10 metal compound are used, high selectivity is achieved in the hydroformylation of an olefin and high catalyst activity is shown even under relatively mild conditions.

The invention claimed is:

1. A bisphosphite represented by formula (I):

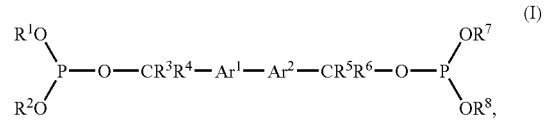

wherein
$Ar^1$ and $Ar^2$ are each independently a substituted or an unsubstituted arylene group;
$R^1$, $R^2$, $R^7$ and $R^8$ are each independently a substituted or an unsubstituted alkyl group, a substituted or an unsubstituted aryl group or a substituted or an unsubstituted heterocyclic group; and
$R^3$, $R^4$, $R^5$ and $R^6$ are each independently a hydrogen atom or an alkyl group, with the proviso that the carbon atom bearing $R^3$ and $R^4$ and the carbon atom bearing $R^5$ and $R^6$ are bound to their respective arylene groups at the ortho position to the $Ar^1$—$Ar^2$ bond.

2. A composition containing a bisphosphite and a Group 8 to 10 metal compound, said bisphosphite represented by formula (I):

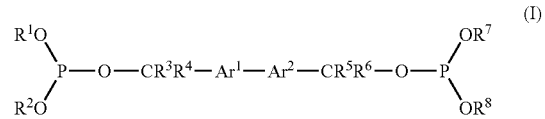

wherein
$Ar^1$ and $Ar^2$ are each independently a substituted or an unsubstituted arylene group;
$R^1$, $R^2$, $R^7$ and $R^8$ are each independently a substituted or an unsubstituted alkyl group, a substituted or an unsubstituted aryl group or a substituted or an unsubstituted heterocyclic group; and
$R^3$, $R^4$, $R^5$ and $R^6$ are each independently a hydrogen atom or an alkyl group, with the proviso that the carbon atom bearing $R^3$ and $R^4$ and the carbon atom bearing $R^5$ and $R^6$ are bound to their respective arylene groups at the ortho position to the $Ar^1$—$Ar^2$ bond.

3. A process for producing an aldehyde, comprising reacting an olefin with carbon monoxide and hydrogen in the presence of a bisphosphite and a Group 8 to 10 metal compound, said bisphosphite represented by formula (I):

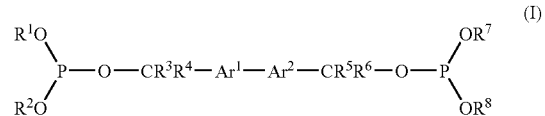

wherein
$Ar^1$ and $Ar^2$ are each independently a substituted or unsubstituted arylene group;
$R^1$, $R^2$, $R^7$ and $R^8$ are each independently a substituted or an unsubstituted alkyl group, a substituted or an unsubstituted aryl group or a substituted or an unsubstituted heterocyclic group; and
$R^3$, $R^4$, $R^5$ and $R^6$ are each independently a hydrogen atom or an alkyl group, with the proviso that the carbon atom bearing $R^3$ and $R^4$ and the carbon atom bearing $R^5$ and $R^6$ are bound to their respective arylene groups at the ortho position to the $Ar^1$—$Ar^2$ bond.

4. The process according to claim 3, wherein said Group 8 to 10 metal compound is a rhodium compound selected from the group consisting of $Rh(acac)(CO)_2$, $RhCl(CO)(PPh_3)_2$, $RhCl(PPh_3)_3$, $RhBr(CO)(PPh_3)_2$, $Rh_4(CO)_{12}$ and $Rh_6(CO)_{16}$.

5. The process according to claim 4, carried out at a temperature of 40 to 150° C.

6. The process according to claim 3, wherein, for every 1 liter of the reaction mixture, the Group 8 to 10 metal compound is used in an amount of 0.0001 to 1000 mmol as measured by the amount of metal atom.

7. The process according to claim 3, wherein the olefin is at least one selected from the group consisting of ethylene, propylene, 1-butene, isobutene, 1-pentene, 1-hexene, 1-heptene, 1-octene, 1-nonene, 1,6-octadiene, 1,7-octadiene, vinylcyclohexene, cyclooctadiene, dicyclopentadiene, cyclopentene, cyclohexene, 1-methylcyclohexene, cyclooctene, limonene, allyl alcohol, crotyl alcohol, 3-methyl-3-buten-1-ol, 7-octen-1-ol, 2,7-octadien-1-ol, vinyl acetate, allyl acetate, methyl acrylate, ethyl acrylate, methyl methacrylate, methyl vinyl ether, allyl ethyl ether, 5-hexenamide, acrylonitrile, 7-octenal, 1-methoxy-2,7-octadiene, 1-ethoxy-2,7-octadiene, 1-propoxy-2,7-octadiene, 1-isopropoxy-2,7-octadiene, styrene, α-methylstyrene, β-methylstyrene, and divinylbenzene.

8. The process according to claim 3, wherein said bisphosphite is at least one selected from the group consisting of:

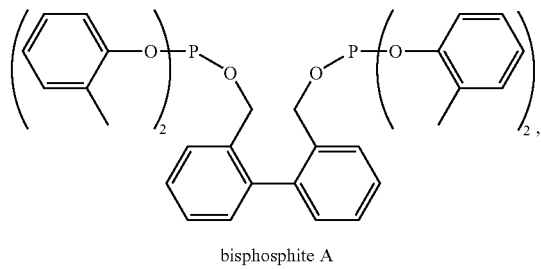

bisphosphite A

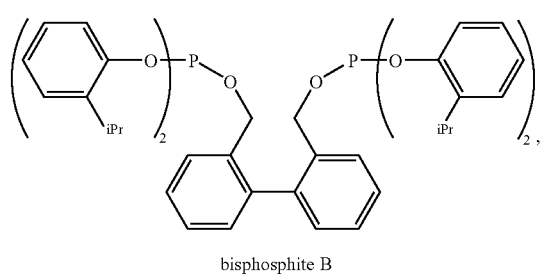

bisphosphite B

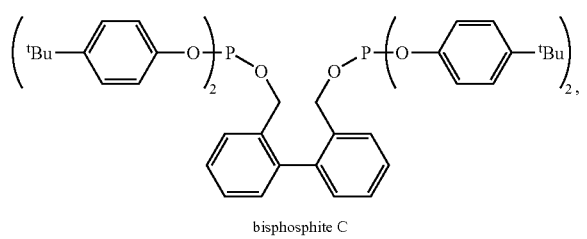

bisphosphite C

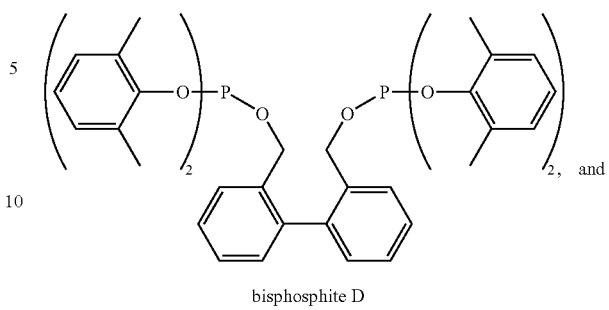

bisphosphite D

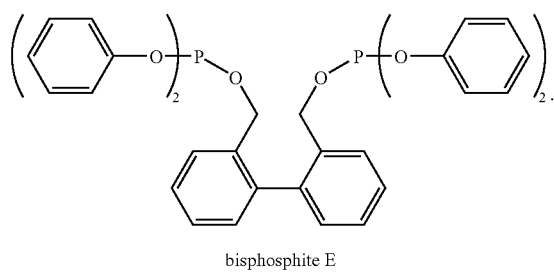

bisphosphite E

9. The composition according to claim 2, wherein said bisphosphite is at least one selected from the group consisting of:

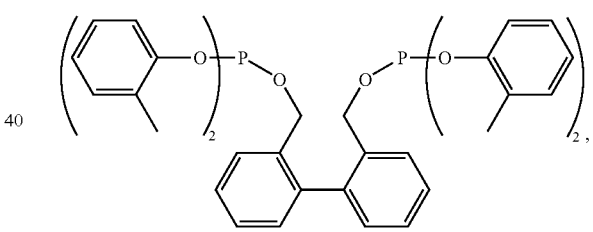

bisphosphite A

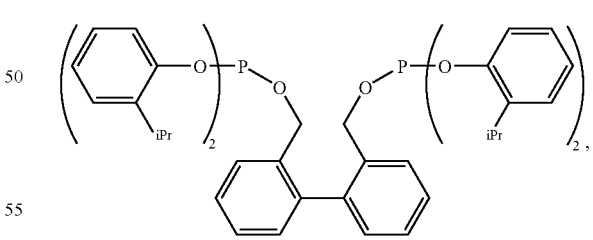

bisphosphite B

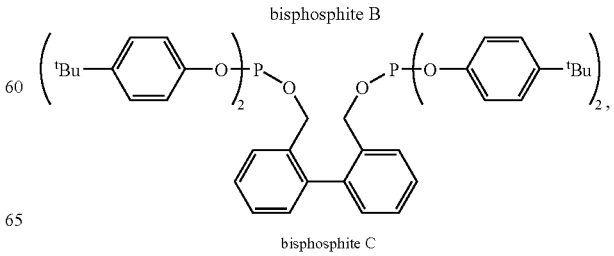

bisphosphite C

-continued
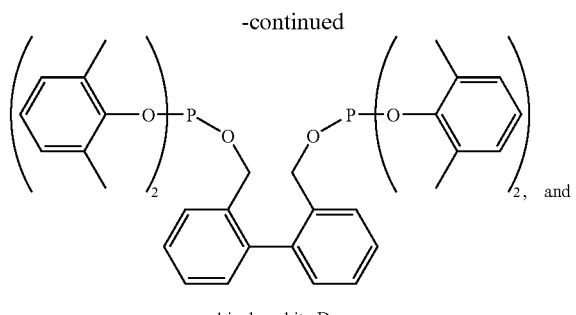
bisphosphite D
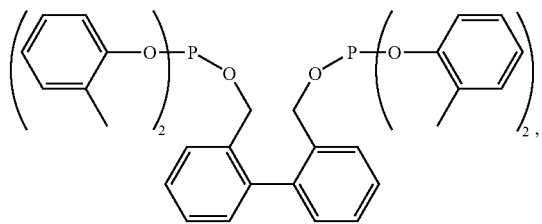
bisphosphite E
10. The bisphosphite according to claim 1, wherein said bisphosphite is at least one selected from the group consisting of:
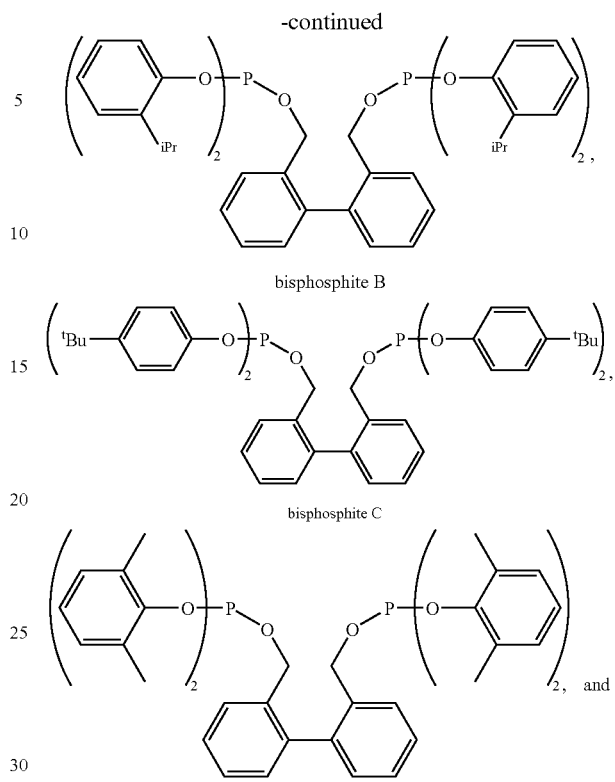
bisphosphite A
bisphosphite B
bisphosphite C
bisphosphite D
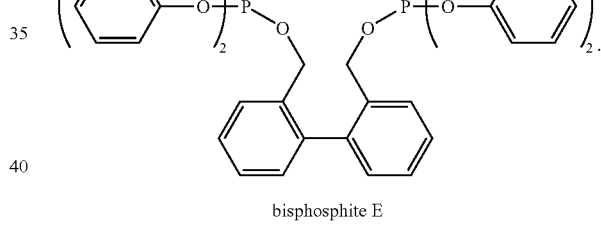
bisphosphite E
* * * * *